United States Patent
Shankar et al.

(10) Patent No.: US 6,411,849 B1
(45) Date of Patent: Jun. 25, 2002

(54) IMPLATABLE ELECTRICAL DEVICE INCORPORATING A MAGNETORESISTIVE-BASED MOTION SENSOR

(75) Inventors: Balakrishnan Shankar, Valencia, CA (US); Kenneth R. McNeil, II, Scottsdale, AZ (US); Alan B. Vogel, Saugus; Scott Gibson, Granada Hills, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/457,279

(22) Filed: Dec. 8, 1999

(51) Int. Cl.[7] .................................................. A61N 1/18
(52) U.S. Cl. ....................................................... 607/19
(58) Field of Search ............................. 600/595; 607/4, 607/5, 7, 9, 11, 17, 19; 73/514.31

(56) References Cited

U.S. PATENT DOCUMENTS

| | | | | |
|---|---|---|---|---|
| 5,025,791 A | * | 6/1991 | Niwa ........................... 128/670 |
| 5,031,615 A | | 7/1991 | Alt .............................. 128/419 |
| 5,425,750 A | | 6/1995 | Moberg ....................... 607/19 |
| 5,454,838 A | * | 10/1995 | Vallana et al. ................ 607/19 |
| 5,842,986 A | * | 12/1998 | Avrin et al. ................. 600/407 |
| 6,044,299 A | * | 3/2000 | Nilsson ........................ 607/19 |
| 6,101,417 A | * | 8/2000 | Vogel et al. .................. 607/30 |

* cited by examiner

Primary Examiner—Jeffrey R. Jastrzab
Assistant Examiner—Frances P. Oropeza

(57) ABSTRACT

An implantable cardiac device including an activity sensor that incorporates a magnetoresistive sensor and a magnet that are positioned so as to move relative to each other in response to activity of the patient when the device is implanted in the body of the patient. In one embodiment, the sensor includes a magnetoresistive sensor that is made from giant magnetoresistive (GMR) materials. In another embodiment, a magnet is positioned on a flexible cantilevered beam so as to be positioned adjacent the magnetoresistive sensor. Movement of the patient results in relative movement of the magnet with respect to the magnetoresistive sensor. The signal can be used by the implantable cardiac device's processor for adjusting the delivery of therapeutic electrical stimulation such as by adjusting the pacing rate of pacing pulses being delivered to the patient's heart.

20 Claims, 4 Drawing Sheets

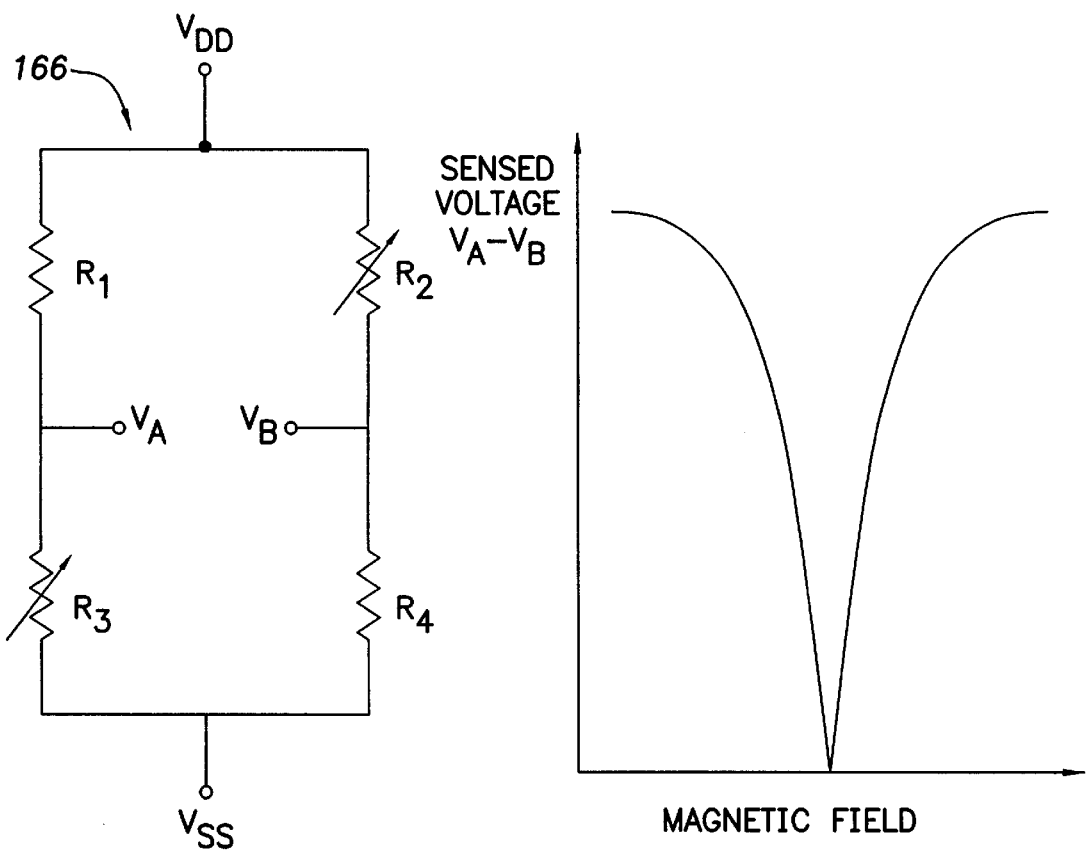
FIG. 3A
FIG. 3B
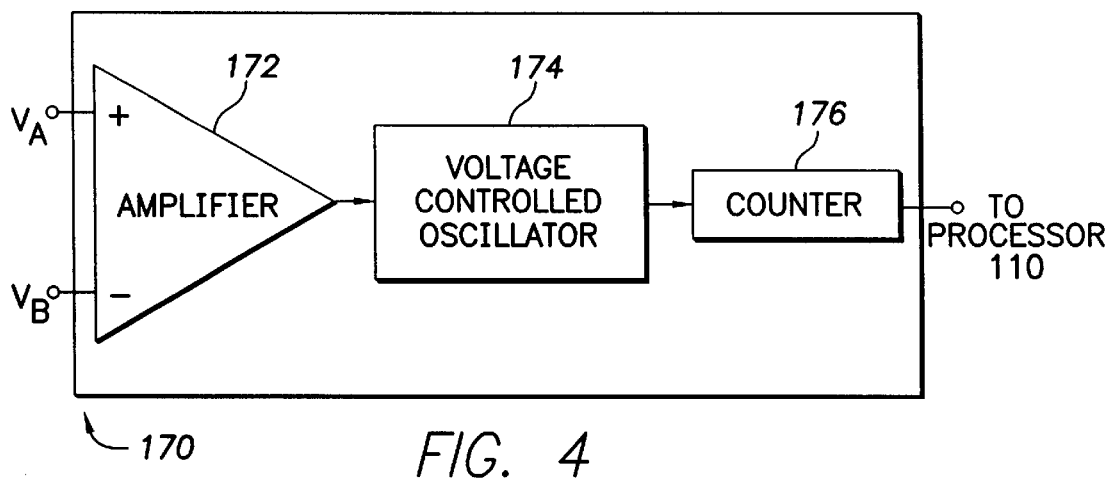
FIG. 4

IMPLATABLE ELECTRICAL DEVICE INCORPORATING A MAGNETORESISTIVE-BASED MOTION SENSOR

FIELD OF THE INVENTION

The present invention relates to implantable electrical devices and, more particularly, an implantable cardiac device that incorporates a magnetoresistive-based motion sensor which is adapted to sense the motion or acceleration of the body of the patient in which the device is implanted.

BACKGROUND OF THE INVENTION

Implantable cardiac devices, such as pacemakers and implantable cardioverter defibrillators (ICDs), have become increasingly sophisticated over the past several years. These devices are now capable of sensing the performance of the heart and responsively applying therapeutic electrical stimulation to the heart that is tailored to correct the heart's performance.

In fact, current generation pacemakers are capable of sensing the activity level of the patient and then tailoring the delivery of pacing pulses to the patient's heart to match the activity level of the patient. For example, if the pacemaker ascertains that the patient is more active, the pacemaker increases the pacing rate so that the patient's heart beats more rapidly to provide an increased flow of blood to the patient. Conversely, when the patient is at rest, the pacemaker decreases the pacing rate so as to maximize the battery life of the pacemaker and also so that the heart rate of the patient more closely mirrors normal function of the heart when the patient is at rest.

Typically, pacemakers and other implantable cardiac devices that provide therapy based at least in part on the activity of the patient, incorporate some sort of an activity sensor. Typically, the activity sensor is comprised of an accelerometer that provides a signal that is indicative of the activity level of the patient. The accelerometer is generally positioned within the implantable cardiac device casing and the accelerometer provides a signal which is indicative of the acceleration experienced by the casing. It is, of course, understood that the greater the activity level of the patient, the more the casing is accelerated. Hence, the accelerometer is capable of providing a signal which is indicative of the activity level of the patient.

Typically, accelerometers that are used in implantable cardiac devices incorporate some sort of piezo-electric sensor. One such accelerometer is described in U.S. Pat. No. 5,425,750 to Moberg. This sensor incorporates a cantilevered beam with a weight mounted on the cantilevered end of the beam. The surface of the beam is coated with a piezo-electric crystal polymer. Acceleration of the casing containing the accelerometer results in the cantilevered beam bending in response to the acceleration. The piezo-electric crystal is mechanically deformed by this bending and thereby produces an electrical signal that is proportionate to the mechanical deformation of the crystal. This electric signal can be amplified and used to provide an indication of the activity level of the patient.

One difficulty associated with using these piezo-electric sensors is that the piezo-electric material is often very expensive. This is particularly true for the very sensitive sensors that have to be used in implantable cardiac devices. The accelerometer as a whole cannot be very large in size as it has to be positioned in the limited confines of an implantable cardiac device casing. Hence, the piezo-electric material must also be relatively small in size which requires the piezo-electric material to be very sensitive in order to be able to provide an electrical signal that is reflective of the acceleration of the pacemaker casing. These types of piezo-electric materials are very expensive and increase the overall cost of the implantable cardiac device.

Also, piezo-electric acceleration sensors are inherently AC coupled. This type of sensor only produces an output proportional to the beam's rate of change of bending and cannot be used to sense the position of the patient's body. Another difficulty associated with the piezo-electric acceleration sensors is that, even though very sensitive piezo-electric materials can be used, the limited amount of space that is taken up by the piezo-electric sensor can still be quite considerable. As the implantable cardiac device casing is implanted within the body, it is desirable to minimize the size of each of the components that are positioned within the casing so as to reduce the overall size of the implantable cardiac device. Unfortunately, the piezo-electric based acceleration sensor must have a certain minimum amount of surface area in order for the material to mechanically deform sufficiently so as to provide a usable signal indicative of the patient's activity level. Consequently, the minimum size of an accelerometer of this type is comparatively large and is not subject to significant reduction in size.

Moreover, the piezoelectric crystals used in these types of activity sensors are under continuous repeated stress. This results in fatigue in the crystalline structure that can, ultimately, result in the activity sensor ceasing to work. It will, of course, be appreciated that replacement of inoperative activity sensors in implanted cardiac devices is impractical if not impossible due to the invasiveness of the procedure.

Hence, there is a need for a sensor which is capable of detecting the activity level of the patient and providing a signal indicative thereof which is both small in size and made of inexpensive components. To this end, there is a need for a sensor which does not require the use of a large amount of surface area, does not require the use of very sensitive piezo-electric materials, and is more resistant to material fatigue related failure.

SUMMARY OF THE INVENTION

The aforementioned needs are satisfied by the sensor of the present invention which is adapted for use with an implantable electrical device. The sensor of the present invention incorporates a magnetoresistive sensor and a magnet that are mounted so as to be movable with respect to each other. Relative movement between the magnet and the magnetoresistive sensor produces a change in the resistance value of the magnetoresistive sensor. This change in the resistance value can be sensed by the application of a voltage to the sensor so that the resulting output signal is indicative of the activity of the patient.

In one aspect of the invention, the magnetoresistive sensor is mounted to a substrate and a permanent magnet is mounted on a bendable cantilevered beam that is attached to the substrate so as to position the permanent magnet in proximity to the magnetoresistive sensor. Movement of the substrate will result in the cantilevered beam bending and vibrating. The movement of the cantilevered beam results in the permanent magnet changing its relative position with respect to the magnetoresistive sensor thereby causing the resistance of the magnetoresistive sensor to change.

In one embodiment of the invention, the magnetoresistive sensor is comprised of a giant magnetoresistive (GMR) sensor that provides a differential output voltage which is indicative of the change of the sensed magnetic field. The output signal varies in both amplitude and frequency and both of these variables can be used by the control unit of an implantable cardiac device as inputs for adjusting and optimizing the delivery of therapeutic electrical stimulation to the heart of the patient.

In another aspect of the invention, an implantable cardiac device is provided which includes a magnetoresistive sensor that provides a signal to a controller which is indicative of the movement of the sensor. The sensor is adapted to be implanted within the body of the patient so that movement of the patient will result in movement of the sensor thereby inducing the sensor to provide the signal to the controller which is indicative of the movement of the patient.

In one embodiment, the sensor is comprised of a magnetoresistive sensor that is fixedly mounted on a substrate and a permanent magnet that is mounted on a cantilevered beam so as to be positioned adjacent the magnetoresistive sensor. The sensor is adapted to be positioned within the body of the patient so that movement of the patient results in the magnet attached to the cantilevered end of the beam moving with respect to the magnetoresistive sensor. The magnetoresistive sensor thereby provides a signal to the controller which is indicative of the movement.

In one aspect of this embodiment of the invention, the magnetoresistive sensor is comprised of a giant magnetoresistive (GMR) sensor which provides an analog voltage to a voltage controlled oscillator. The voltage controlled oscillator provides an output signal to a counter which counts the oscillation signal provided by the voltage controlled oscillator. The output of the counter is then sampled by the implantable cardiac device's processor which provides the processor with a signal that is indicative of both the amplitude and the frequency of the movement sensed by the sensor.

It will be appreciated that the processor can then use this information to change the therapeutic electrical stimulation that is being applied to the heart of the patient. For example, if the frequency and amplitude of the signal from the sensor suggests the patient is engaged in more rigorous physical activity, the processor can use this information to increase the pacing rate of a pacemaker to enable the heart to pump more blood to the body's extremities. Conversely, when the acceleration signal indicates that the patient is at rest, the processor can then reduce the pacing rate so as to conserve battery power and also so as to have the heart performance more closely mirror the normal heart performance when the patient is at rest.

By using a magnetoresistive sensor as opposed to a piezo-electric element, the preferred activity sensor can be smaller in size, less expensive to manufacture and less prone to subsequent failure. These and other objects of the present invention will become more fully apparent from the following description taken in conjunction with the accompanying drawings.

BRIEF DESCRIPTION OF THE DRAWINGS

FIG. 3A is an electrical block diagram illustrating one configuration of the magnetoresistive activity sensor of FIGS. 2A–2C;

FIG. 3B is a reproduced chart illustrating a typical performance curve of the magnetoresistive activity sensor of FIG. 3A;

FIG. 4 is an electrical block diagram illustrating an acceleration sensor circuit of the implantable electrical device of FIG. 1.

DETAILED DESCRIPTION OF THE PREFERRED EMBODIMENT

Figure 1:
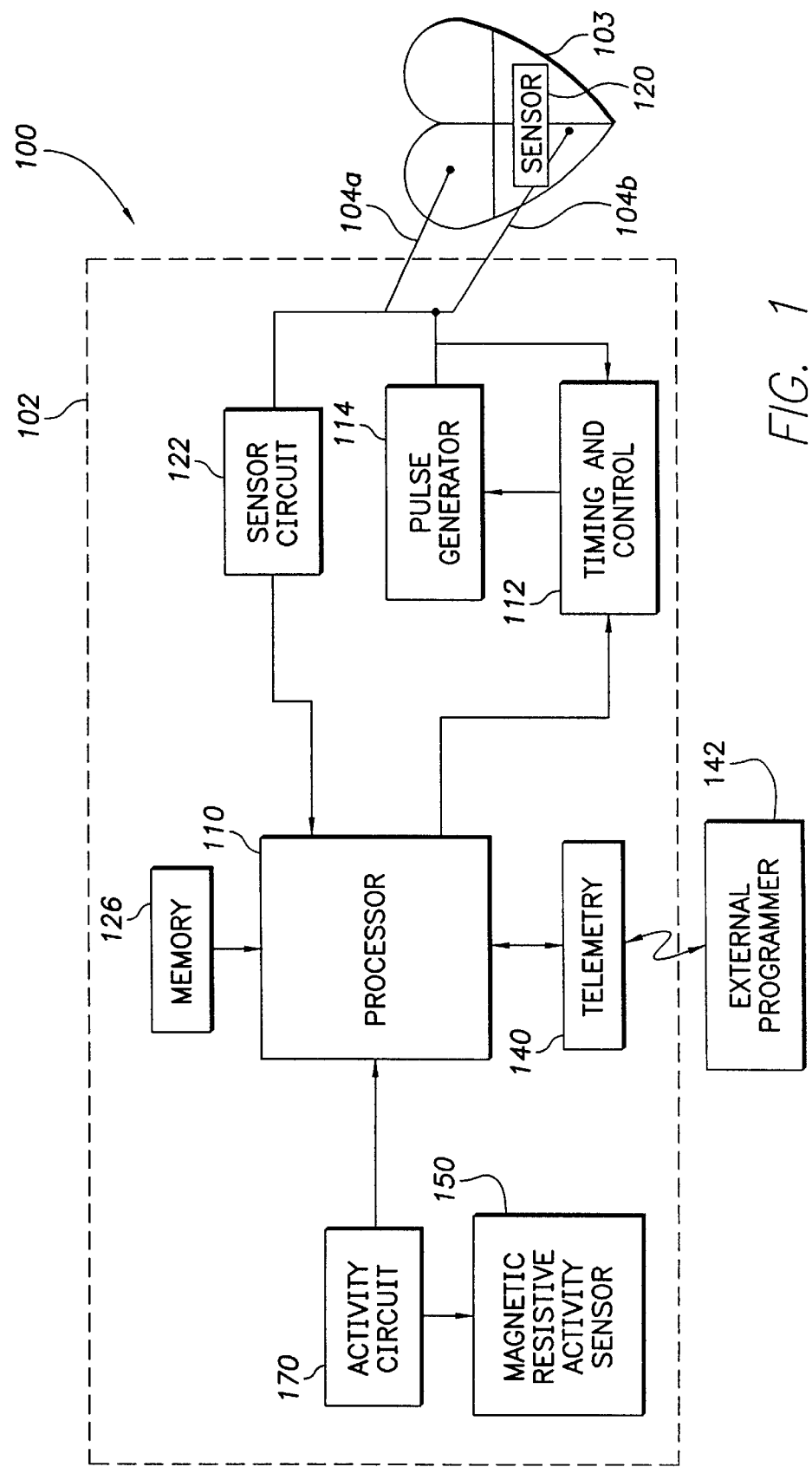
FIG. 1 is a block diagram of one embodiment of an implantable cardiac device incorporating a magnetoresistive based activity sensor.

Reference will now be made to the drawings wherein like numerals refer to like parts throughout. Referring initially to FIG. 1, one embodiment of an implantable cardiac device 100 is shown. The implantable electrical device 100 incorporates a control unit, generally designated 102, and a plurality of leads 104 that are configured to be positioned within the chambers of a patient's heart 103. In the embodiment shown in FIG. 1, the implantable cardiac device 100 includes a first lead 104a that is configured to be implanted within an atrium of the heart 103 and a second lead 104b that is configured to be implanted within a ventricle of the heart 103.

The implantable cardiac device 100 can be comprised of any implantable device including a pacemaker or an implantable cardioverter defibrillator (ICD) or some implantable device incorporating the functionality of both a pacemaker and an ICD.

The control unit 102 is preferably positioned within a casing that is also adapted to be implanted within the body of the patient. In one application, the control unit 102 is positioned within a casing that is designed to be implanted underneath the pectoral muscle of the patient and the leads 104 are designed to be inserted into the chambers of the heart 103 using well-known pectoral implant techniques.

The control unit 102 includes a processor 110 which provides output signals to a timing and control circuit 112. Upon receipt of the output signals from the processor 110, the timing and control circuit 112 causes a pulse generator 114 to produce therapeutic electrical stimulation that is transported via the leads 104 to thereby stimulate the heart 103. The exact function of the processor 110 in inducing the delivery of the therapeutic electrical stimulation to the heart is performed in any of a number of well-known manners. For example, in one operational mode, the processor 110 induces pacing pulses to be delivered to the apex of the ventricle of the heart 103.

Further, the processor 110 receives input signals from a sensor 120 via a sensor circuit 122. In one embodiment, the sensor 120 is actually comprised of an implanted lead that is positioned within one of the chambers of the heart 103 so as to provide an intra-cardiac electrogram (IEG) signal to the processor 110 in a well-known manner. Hence, the processor 110 is configured to receive a signal which is indicative of the activity of the heart 103 and is further configured to provide therapeutic electrical stimulation to the heart based, at least in part, upon the IEG signal.

Further, as will be discussed in greater detail below, the control unit also includes an activity sensor 150 that provides the processor 110, via the activity circuit 170, input signals that are indicative of the activity of the patient. The processor 110 uses the input signals from the sensor 150 to adjust the therapeutic electrical stimulation that is being provided to the heart 103 via the leads 104.

For example, in the application of a pacemaker, the sensor 150 provides an input signal to the processor 110 which is indicative of the activity level of the patient. When the patient is particularly active, the activity sensor 150 provides a corresponding signal to the processor 110 and the processor 110 uses this signal to increase the pacing rate of the pacemaker to thereby induce the heart 103 to beat faster thereby providing more blood to the patient's muscles. Alternatively, when the activity sensor 150 indicates that the patient is at rest, the processor 110 reduces the pacing rate so as to conserve power and also so as to have the heart 103 perform in a manner which more closely mirrors the operation of normal hearts when the patient is at rest.

The processor 110 of the embodiment shown in FIG. 1 is also capable of communicating via a telemetry circuit 140 with an external programmer 142. As is understood in the art, the telemetry circuit 140 typically includes an RF signal generator and an RF signal receiver that communicates with a matching RF signal generator and RF signal receiver on the programmer 142. Instructions can be downloaded into the processor 110 to configure the processor 110 to provide particular types of therapy to the heart 103. Further, information and data stored in the memory 126 can be uploaded by the processor 110 via the telemetry circuit 140 to the external programmer 142. This allows treating physicians to retrieve information stored in the memory 126 indicative of the functioning of the implantable electrical device or the heart 103 during particular episodes.

In the foregoing aspects, the general function and operation of the implantable cardiac device 100 is substantially the same as the function and operation of similar implantable cardiac devices of the prior art. Thus, a person of ordinary skill in the art will appreciate that the configuration of the implantable cardiac device shown in FIG. 1 is simply illustrative of one possible configuration and the exact configuration and operation of the device can vary from patient to patient without departing from the spirit of the present invention.

Figure 2A:
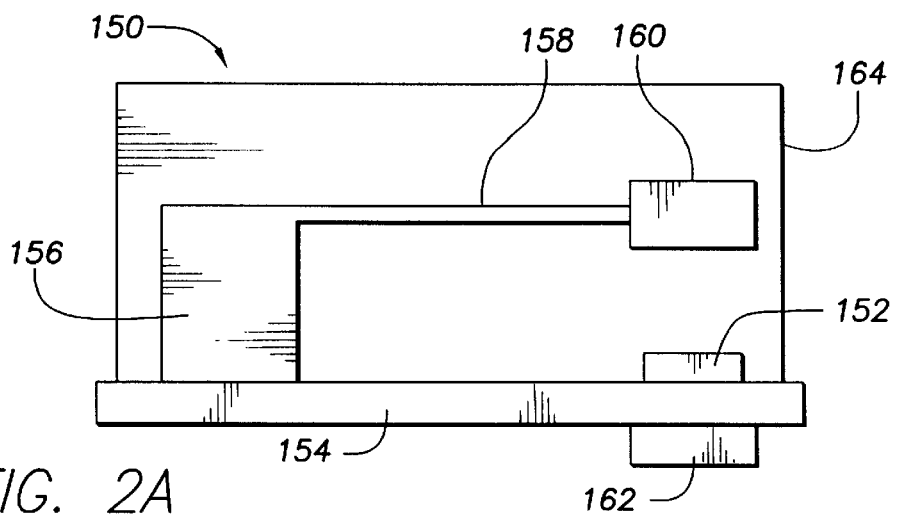
FIG. 2A is a side view illustrating one embodiment of a magnetoresistive activity sensor of the preferred embodiment.
Figure 2B:
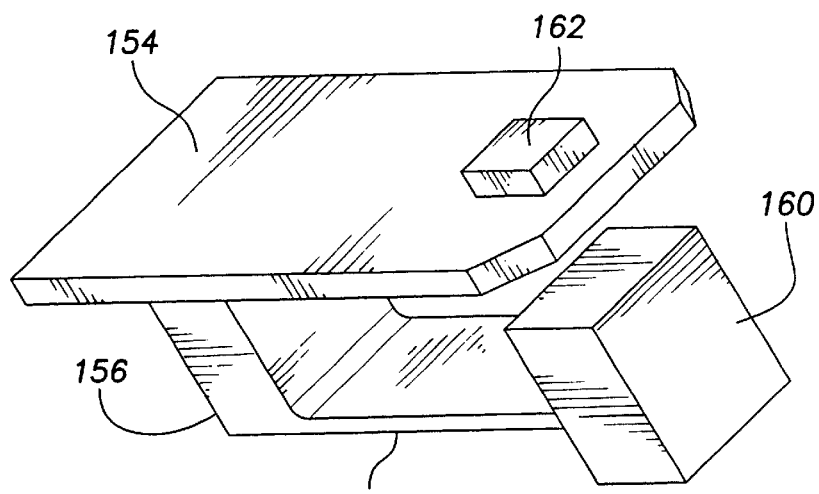
FIG. 2B is a perspective view which illustrates the magnetoresistive activity sensor of FIG. 2A from a first perspective.
Figure 2C:
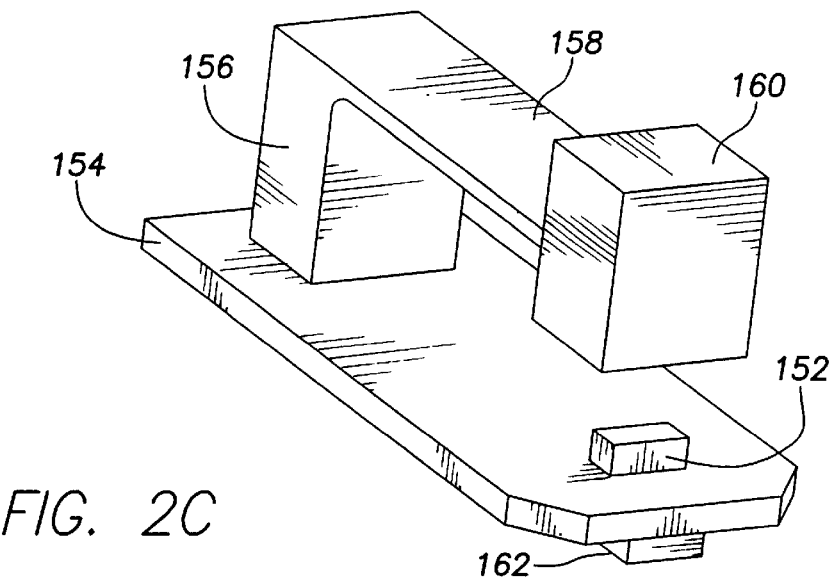
FIG. 2C is a perspective view which illustrates the magnetoresistive activity sensor of FIG. 2A from a second perspective.

Referring to FIGS. 2A–2C, the magnetoresistive activity sensor assembly 150 of FIG. 1 will be described in greater detail. In particular, the assembly 150 includes a magnetoresistive sensor 152 that is mounted on a first side of a substrate 154. Also mounted on the first side of the substrate 154 is a mounting block 156. A cantilevered member 158 extends outward from the mounting block 156 so as to be positioned adjacent the magnetoresistive sensor 152. A permanent magnet 160 is mounted on the cantilevered end of the cantilevered member 158 so as to be positioned generally over the magnetoresistive sensor 152. The cantilevered member 158 is preferably made of a flexible material so that movement of the sensor assembly 150 will result in the cantilevered member 158 vibrating with respect to the mounting block 156, thereby allowing the permanent magnet 160 to move relative the magnetoresistive sensor 152.

The movement of the magnet 160 with respect to the magnetoresistive sensor 152 results in the magnetoresistive sensor 152 producing an electrical signal that is proportionate to the magnetic field that is sensed by the magnetoresistive sensor 152. It will be appreciated that the magnetic field, as seen by the sensor 152, will increase as the magnet 160 moves towards the magnetoresistive sensor 152 and will decrease as the magnet 160 moves away from the magnetoresistive sensor 152.

As is also shown in FIGS. 2A–2C, the sensor assembly 150 preferably includes an offset magnet 162 that is mounted on the second side of the substrate 154 so as to be positioned substantially opposite the magnetoresistive sensor 152. The strength of the offset magnet 162 and the magnet 160 are selected so that when the sensor assembly 150 is implanted within the body of the patient and the body of the patient is at rest, the combined magnetic fields of the offset magnet 162 and the magnet 160 preferably create an effectively zero magnetic field at the location of the magnetoresistive sensor 152. When the patient is in motion, the cantilevered member 158 with the magnet 160 mounted thereon moves, which creates a differential magnetic field that is sensed by the magnetoresistive sensor 152.

As is also illustrated in FIG. 2A, the sensor assembly 150 preferably includes a sensor shield 164 that is positioned about the first face of the substrate 152 so as to enclose the magnetoresistive sensor 152 and the magnet 160. In this way, the effect of stray magnetic fields on the magnetoresistive sensor 152 is reduced.

FIG. 3A is an exemplary electrical schematic which illustrates a bridge circuit 166 that comprises the magnetoresistive sensor 152. In particular, the bridge circuit 166 of this embodiment receives a supply voltage $V_{DD}$ and a ground voltage $V_{SS}$ with two parallel sets of two resistors in series $R_1$ and $R_3$ and $R_2$ and $R_4$, respectively. The output voltage of the bridge, $V_A$ and $V_B$ is obtained at a point between the series resistors $R_1$ and $R_3$, and $R_2$ and $R_4$, respectively.

As shown in FIG. 3A, the resistors $R_2$ and $R_3$ are comprised of resistors made of a magnetoresistive material and, in particular, are resistors that are made of giant magnetoresistive ratio (GMR) materials. The two resistors $R_2$ and $R_3$ exhibit a magnetoresistive effect whereby the measured resistance values of the resistors $R_2$ and $R_3$ change in response to changes in the magnitude of the applied magnetic field. The resistors $R_2$ and $R_3$ are preferably positioned near flux concentrators (not shown) so that the change in magnetic field strength is more strongly reflected in the change of the resistance of these resistors. This change in the resistance of $R_2$ and $R_3$ result in voltages that are seen at $V_A$ and $V_B$ varying correspondingly. In this embodiment, the resistors $R_1$ and $R_4$ are also made of GMR material but are shielded so as to not be as sensitive to changes in magnetic flux.

Hence, the variations of the magnetic field produced by the magnet 160 as a result of induced movement of the cantilevered member 158 results in the magnetoresistive material forming the resistors $R_2$ and $R_3$ having varying resistance values and thereby also results in the voltages $V_A$ and $V_B$ also having varying values. A differential voltage signal $V_A - V_B$ can therefore be used as the magnetic field signal since this differential voltage signal varies over a range of values depending upon the magnitude of the sensed magnetic field.

In a preferred embodiment, the circuit 166 is a giant magnetoresistive sensor (GMR) bridge such as that provided by Nonvolatile Electronics, Inc. of Eden Prairie, Minn. The typical operating characteristics for the GMR sensor used in this embodiment is shown in FIG. 3B. In particular, for the illustrated sensor, the differential output voltage $V_A - V_B$ of the circuit 166 is plotted in FIG. 3B versus the applied field. As shown in FIG. 3B, the output signal from the bridge circuit 166 is linear for approximately 70 percent of the full range of the applied fields and a peak signal occurs at the saturation level of the device. Hence, the circuit 166 is capable of providing a range of voltage values that is indicative of the strength of the magnetic field.

FIG. 4 is an exemplary block diagram of the activity circuit 170. The activity circuit 170 receives the differential voltage $V_A$ and $V_B$ and amplifies this voltage via a differential voltage amplifier 172. The output of the amplifier is then provided to a voltage controlled oscillator 174 which then oscillates at a frequency which is directly proportional to the input voltage. The circuit 170 also includes a digital counter 176 which increments based upon the output of the voltage controlled oscillator 174. The counter 176 therefore provides a digital value which is related to the magnitude and frequency of the differential voltage $V_A-V_B$ that has been provided by the sensor circuit 166. It will be understood that the value provided by the counter 176 is indicative of the integral of the amplitude of the differential voltage $V_A-V_B$ over time. The value of the counter 176 can then be used by the processor 110 to adjust the therapeutic electrical stimulation that is being provided to the heart 103 via the leads 104.

Figure 5:
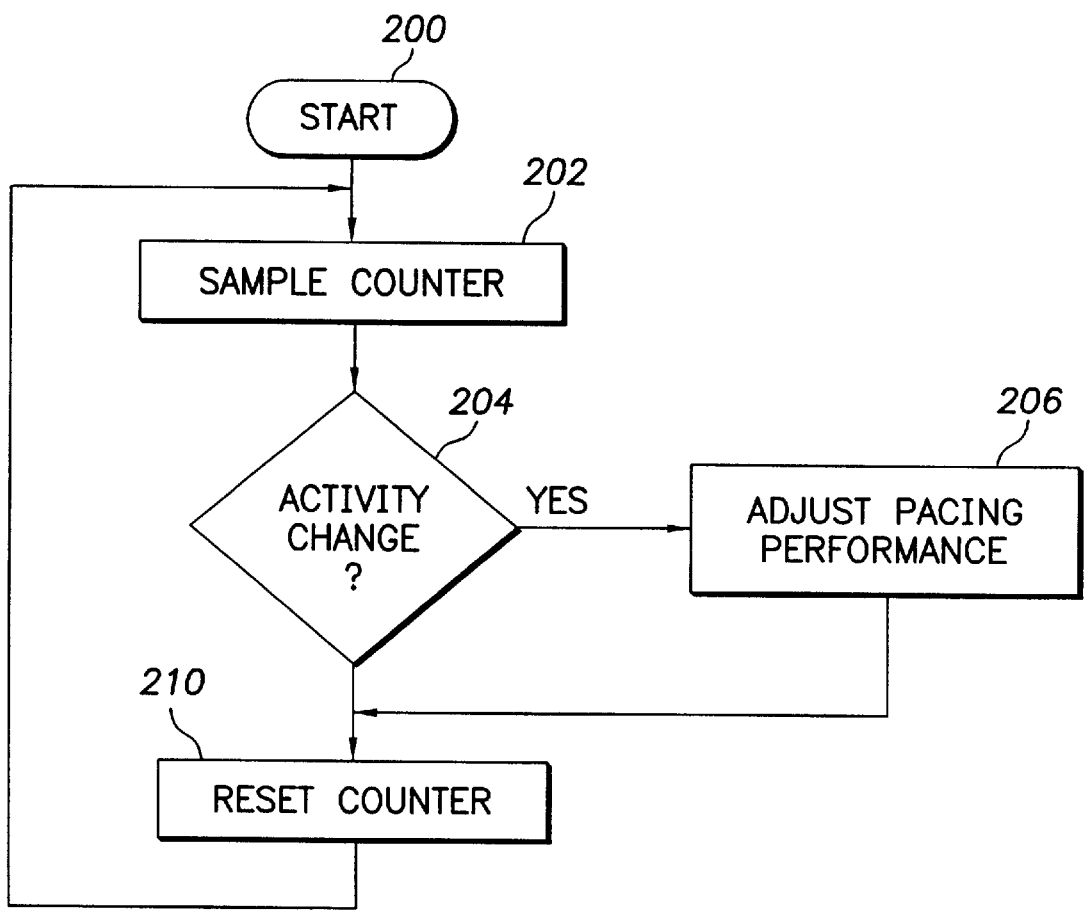
FIG. 5 is a flow chart illustrating the operation of the implantable cardiac device of FIG. 1 in conjunction with the magnetoresistive activity sensor of FIGS. 2A–2C.

In particular, FIG. 5 is a simplified flow chart which illustrates the operation of the processor 110 as it samples the counter value. In particular, the processor 110 from a start state 200 proceeds to a state 202 where it samples the digital value of the counter 176. In the preferred embodiment, the counter 176 is sampled approximately once every second or once every pacing pulse. Once the processor 110 has sampled the counter 176, the processor 110 then determines in decision state 204 whether the counter value is indicative of an activity change.

The frequency and amplitude of the signal $V_A-V_B$ varies as a result of the activity level of the patient. As the counter value is proportionate to the integral of these values, any change in the activity level of the patient is sensed by the processor 110 when the processor 110 samples the counter value. If the processor 110 determines that the counter value is indicative of a change in the patient's activity level, the electrical stimulation that is provided to the heart via the pulse generator 114 and the leads 104 (see FIG. 1) can be adjusted in state 206. For example, if the counter value is indicative of very little physical activity on the part of the patient, the processor 110 may slow down the frequency of delivery of pacing pulses to the heart to thereby slow the patient's heart down and also to reduce the drain on the battery. Alternatively, if the value in the counter 176 is indicative of heightened physical activity, the processor 110 can increase the pacing rate to increase the heart rate of the patient to accommodate the greater physical activity.

It will be understood that the adjustment in the pacing rate of the implantable cardiac device can be performed using well-known techniques. Once the pacing performance has been adjusted, the processor then resets the counter 176 in state 210 and returns to sample the counter 176 in the state 202 in the manner described above.

Hence, the implantable electrical device incorporating the sensor of the preferred embodiment is capable of adjusting the delivery of therapeutic electrical stimulation, such as pacing pulses, based upon the signal that is provided by the sensor. The sensor is adapted to be implanted within the body of the patient so that movement of the patient results in corresponding movement of the sensor. As the sensor is a magnetoresistive sensor, as opposed to a piezo-electric crystal, the likelihood of a failure due to repeated use is reduced. Further, the magnetoresistive sensor is comparatively small in size which means that less space within the implantable cardiac device is taken up by the activity sensor.

Although the foregoing description of the preferred embodiment of the present invention has shown, described and pointed out the fundamental novel features of the invention, it will be understood that various omissions, substitutions and changes in form of the detail of the apparatus as illustrated as well as the uses thereof, may be made by those skilled in the art without departing from the spirit from the present invention. For example, while the use of a permanent magnet on a cantilevered beam moving relative to a magnetoresistive sensor has been shown, the converse construction is also considered to be within the scope of the present invention. For example, embodiments of the present invention also include placement of the magnetoresistive sensor on a cantilevered beam that moves relative to a permanent magnet that is fixed to a substrate or alternatively surrounds at least a portion of the magnetoresistive sensor. Consequently, the scope of the invention should not be limited to the foregoing discussion, but should be defined by the appended claims.

What is claimed is:

1. An implantable cardiac device contained within a casing and adapted to be implanted in the body of a patient, the device comprising:

delivery means for delivering therapeutic electrical stimulation to the heart of the patient;

control means for controlling the delivery of therapeutic electrical stimulation to the heart of the patient; and an activity sensor incorporating a first magnet and a magnetoresistive sensor, the activity sensor being adapted to be implanted in the body of the patient so that movement of the patient results in relative movement between the first magnet and the magnetoresistive sensor so that the magnetoresistive sensor provides a variable activity signal that is indicative of the activity of the patient; and wherein the control means controls the delivery of therapeutic electrical simulation to the heart of the patient responsive, at least in part, to the variable activity signal; and means for generating a magnetic field to produce a substantially zero magnetic field at the magnetoresistive sensor when the first magnet is at rest.

2. The device of claim 1, wherein the delivery means comprises at least one lead that is adapted to be positioned adjacent to the wall of the heart and is further adapted to deliver pacing pulses to the heart.

3. The device of claim 2, wherein the control means comprises a processor that is positioned within the casing, wherein the processor is adapted to receive the variable activity signal and to use the variable activity signal to adjust the frequency of the pacing pulses that are to be delivered to the heart via the at least one lead.

4. The device of claim 3, wherein the control means is adapted to increase the pacing rate of pacing pulses that are delivered to the heart when the variable activity signal indicates that the patient is more active.

5. The device of claim 1, wherein the activity sensor additionally comprises:

a substrate having a first and a second surface that is positioned within the casing of the implantable cardiac device wherein the magnetoresistive sensor is mounted on the substrate;

and wherein the first magnet is movably mounted proximate to the substrate so that when the casing is implanted in the body of a patient, activity of the patient results in the magnet moving with respect to the magnetoresistive sensor so that the magnetoresistive sensor produces the variable activity signal that is proportional to the movement of the magnet with respect to the magnetoresistive sensor.

6. The device of claim 5, wherein the activity sensor further comprises:
   a mounting block that is positioned on the first surface of the substrate; and
   a flexible cantilevered beam that is attached to the mounting block so that the flexible cantilevered beam extends outward from the mounting block; and wherein
   the first magnet is mounted on the outer end of the flexible cantilevered beam so as to be positioned adjacent the magnetoresistive sensor.

7. The device of claim 6, wherein the means for generating a magnetic field comprises a second magnet that is positioned on the second surface of the substrate, wherein the second magnet is selected so that when the first magnet is positioned adjacent the magnetoresistive sensor and is at rest, the combined magnetic field of both the first magnet and the second magnet is substantially zero at the magnetoresistive sensor.

8. The device of claim 7, wherein the magnetoresistive sensor is formed out of giant magnetoresistive (GMR) materials.

9. The device of claim 1, wherein the magnetoresistive sensor is comprised of a bridge circuit having at least one resistor formed out of giant magnetoresistive (GMR) materials.

10. The device of claim 9, further comprising an activity circuit that receives an output voltage signal from the bridge circuit and provides an input signal to the control means that is indicative of the relative movement between the first magnet and the magnetoresistive sensor.

11. The device of claim 10, wherein the input signal comprises the variable activity signal and the variable activity signal received by the control means is indicative of both the frequency and magnitude of the relative motion of the first magnet and the magnetoresistive sensor.

12. The device of claim 10, wherein the activity circuit comprises:
    a voltage controlled oscillator that receives the output signal from the bridge circuit and oscillates at a frequency that is proportional to the magnitude of the voltage provided by the bridge circuit; and
    a counter which receives an output signal of the voltage controlled oscillator and provides a digital signal indicative of the oscillations of the voltage controlled oscillator; and wherein
    the control means periodically samples the counter value so that the counter value comprises the variable activity signal.

13. An implantable cardiac device adapted to be implanted in the body of a patient, the device comprising:
    a casing adapted to be implanted within the body of a patient;
    a controller for controlling the delivery of therapeutic electrical stimulation to the heart of the patient;
    a first magnet positioned within the casing;
    a magnetoresistive sensor positioned within the casing, wherein the first magnet and the magnetoresistive sensor are mounted so as to be moveable with respect to each other; wherein
    the magnetoresistive sensor produces a first signal that is indicative of the magnetic field sensed by the magnetoresistive sensor such that the first signal is indicative of the relative motion between the first magnet and the magnetoresistive sensor; and
    an activity circuit that receives the first signal and provides a corresponding activity signal to the controller so as to allow the controller to adjust the delivery of therapeutic electrical stimulation to the heart of the patient responsive, atileast in part, to the activity signal; and
    a second magnet that is positioned on the second surface of the substrate, wherein the strength of the second magnet is selected so that when the first magnet is positioned adjacent the magnetoresistive sensor and is at rest, the combined magnetic field of both the first magnet and the second magnet is substantially zero at the magnetoresistive sensor.

14. The device of claim 13, wherein the activity signal received by the controller is indicative of both the frequency and magnitude of the relative motion of the first magnet and the magnetoresistive sensor.

15. The device of claim 14, wherein the activity circuit comprises:
    a voltage controlled oscillator that receives the output signal from the bridge circuit and oscillates at a frequency that is proportional to the magnitude of the voltage provided by the bridge circuit; and
    a counter which receives the output signal of the voltage controlled oscillator and provides a digital signal indicative of the oscillations of the voltage controlled oscillator and wherein the controller periodically samples the counter value so that the counter value comprises the variable activity signal.

16. The device of claim 13, further comprising a substrate positioned within the casing the substrate having a first and a second surface wherein the magnetoresistive sensor is mounted on the substrate and wherein the first magnet is movably mounted to the substrate so that when the casing is implanted in the body of a patient, activity of the patient results in the first magnet moving with respect to the magnetoresistive sensor so that the magnetoresistive sensor produces the first signal that is indicative of the movement of the first magnet with respect to the magnetoresistive sensor.

17. The device of claim 15, further comprising:
    a mounting block that is positioned on the first surface of the substrate; and
    a flexible cantilevered beam that is attached to the mounting block so that the flexible cantilevered beam extends outward from the mounting block wherein the first magnet is mounted on the outer end of the flexible cantilevered beam so as to be positioned adjacent to the magnetoresistive sensor.

18. The device of claim 13, wherein the magnetoresistive sensor is comprised of a magnetoresistive sensor formed out of giant magnetoresistive (GMR) materials.

19. The device of claim 13, wherein the magnetoresistive sensor is comprised of a bridge circuit having at least one resistor formed out of giant magnetoresistive (GMR) materials.

20. The device of claim 13, wherein the controller is adapted to increase the pacing rate of pacing pulses that are delivered to the heart when the activity signal indicates that the patient is more active.

\* \* \* \* \*